US008062336B2

(12) United States Patent
Triplett et al.

(10) Patent No.: US 8,062,336 B2
(45) Date of Patent: Nov. 22, 2011

(54) POLYAXIAL ORTHOPEDIC FASTENING APPARATUS WITH INDEPENDENT LOCKING MODES

(75) Inventors: Daniel J. Triplett, Providence, UT (US); Joel R. Helgerson, Providence, UT (US); Robert W. Hoy, Columbus, OH (US)

(73) Assignee: GMEDELAWARE 2 LLC, Audubon, PA (US)

( * ) Notice: Subject to any disclaimer, the term of this patent is extended or adjusted under 35 U.S.C. 154(b) by 1204 days.

(21) Appl. No.: 11/312,323

(22) Filed: Dec. 19, 2005

(65) Prior Publication Data

US 2006/0212034 A1      Sep. 21, 2006

Related U.S. Application Data

(63) Continuation-in-part of application No. 11/063,941, filed on Feb. 22, 2005, now Pat. No. 7,993,373.

(51) Int. Cl.
*A61B 17/70* (2006.01)
(52) U.S. Cl. ......... 606/247; 606/272; 606/306; 606/313
(58) Field of Classification Search ............ 606/60, 606/246, 250–279, 300–321; 623/17.11–17.16; 411/58, 537, 380, 401
See application file for complete search history.

(56) References Cited

U.S. PATENT DOCUMENTS

| 2,677,369 A | 5/1954 | Knowles |
| 3,247,000 A | 4/1966 | Taylor |
| 3,298,372 A | 1/1967 | Feinberg |
| 3,426,364 A | 2/1969 | Lumb |
| 3,486,505 A | 12/1969 | Morrison |
| 3,508,954 A | 4/1970 | White et al. |
| 3,648,691 A | 3/1972 | Lumb et al. |
| 3,857,642 A | 12/1974 | Miller |
| 3,867,728 A | 2/1975 | Stubstad et al. |
| 3,875,595 A | 4/1975 | Froning |
| 4,003,376 A | 1/1977 | McKay |
| 4,092,078 A | 5/1978 | Klotz et al. |
| 4,289,123 A | 9/1981 | Dunn |
| 4,349,921 A | 9/1982 | Kuntz |
| 4,369,769 A | 1/1983 | Edwards |
| 4,479,491 A | 10/1984 | Martin |

(Continued)

FOREIGN PATENT DOCUMENTS

EP          408489 A1      1/1991

(Continued)

OTHER PUBLICATIONS

Goh JC, et al., "Influence of PLIF cage size on lumbar spine stability", Spine, Jan. 2000 25:1, PubMed abstract.

(Continued)

*Primary Examiner* — Eduardo C Robert
*Assistant Examiner* — Jerry Cumberledge

(57) ABSTRACT

An apparatus is designed to attach an implant to bone in a manner that permits rotational adjustment of the implant about multiple axes prior to securement via the apparatus. The apparatus includes separate rotational and translational fasteners that can be individually locked to independently restrict rotation and translation of the implant relative to the bone. The rotational fastener includes an interpositional member, an expandable engagement member, and a rotational locking member that urges the expandable engagement member to advance along the interpositional member. The resulting expansion of the engagement member causes it to engage the implant. The rotational fastener is slidable along a fixation member implanted in the bone until the translational fastener is applied to restrict relative translation between the rotational fastener and the bone.

12 Claims, 3 Drawing Sheets

U.S. PATENT DOCUMENTS

| | | | |
|---|---|---|---|
| 4,483,334 A | 11/1984 | Murray | |
| 4,501,269 A | 2/1985 | Bagby | |
| 4,554,914 A | 11/1985 | Kapp et al. | |
| 4,599,086 A | 7/1986 | Doty | |
| 4,604,995 A | 8/1986 | Stephens et al. | |
| 4,611,581 A | 9/1986 | Steffee | |
| 4,641,636 A | 2/1987 | Cotrel | |
| 4,653,481 A | 3/1987 | Howland et al. | |
| 4,657,550 A | 4/1987 | Daher | |
| 4,696,290 A | 9/1987 | Steffee | |
| 4,743,260 A | 5/1988 | Burton | |
| 4,759,769 A | 7/1988 | Hedman et al. | |
| 4,772,287 A | 9/1988 | Ray et al. | |
| 4,790,303 A | 12/1988 | Steffee | |
| 4,800,874 A | 1/1989 | David et al. | |
| 4,805,602 A | 2/1989 | Puno et al. | |
| 4,827,918 A | 5/1989 | Olerud | |
| 4,863,476 A | 9/1989 | Shepperd | |
| 4,863,477 A | 9/1989 | Monson | |
| 4,892,545 A | 1/1990 | Day et al. | |
| 4,904,260 A | 2/1990 | Ray et al. | |
| 4,911,718 A | 3/1990 | Lee et al. | |
| 4,946,458 A | 8/1990 | Harms et al. | |
| 4,955,908 A | 9/1990 | Frey et al. | |
| 5,011,484 A | 4/1991 | Breard | |
| 5,015,255 A | 5/1991 | Kuslich | |
| 5,047,029 A * | 9/1991 | Aebi et al. | 606/264 |
| 5,047,055 A | 9/1991 | Bao et al. | |
| 5,071,437 A | 12/1991 | Steffee | |
| 5,092,866 A | 3/1992 | Breard et al. | |
| 5,092,867 A | 3/1992 | Harms et al. | |
| 5,092,893 A | 3/1992 | Smith | |
| 5,127,912 A | 7/1992 | Ray et al. | |
| 5,129,900 A | 7/1992 | Asher et al. | |
| 5,147,361 A | 9/1992 | Ojima et al. | |
| 5,147,404 A | 9/1992 | Downey | |
| 5,171,279 A | 12/1992 | Mathews | |
| 5,171,280 A | 12/1992 | Baumgartner | |
| 5,180,393 A | 1/1993 | Commarmond | |
| 5,192,326 A | 3/1993 | Bao et al. | |
| 5,236,460 A | 8/1993 | Barber | |
| 5,246,458 A | 9/1993 | Graham | |
| 5,258,031 A | 11/1993 | Salib et al. | |
| 5,261,910 A | 11/1993 | Warden et al. | |
| 5,263,953 A | 11/1993 | Bagby | |
| 5,282,863 A | 2/1994 | Burton | |
| 5,304,178 A | 4/1994 | Stahurski | |
| 5,306,275 A | 4/1994 | Bryan | |
| 5,306,308 A | 4/1994 | Gross et al. | |
| 5,306,309 A | 4/1994 | Wagner et al. | |
| 5,313,962 A | 5/1994 | Obenchain | |
| 5,318,567 A | 6/1994 | Vichard | |
| 5,360,430 A | 11/1994 | Lin | |
| 5,366,455 A | 11/1994 | Dove et al. | |
| 5,370,697 A | 12/1994 | Baumgartner | |
| 5,375,823 A | 12/1994 | Navas | |
| 5,387,213 A | 2/1995 | Breard et al. | |
| 5,391,168 A | 2/1995 | Sanders et al. | |
| 5,401,269 A | 3/1995 | Buttner-Janz et al. | |
| 5,415,661 A | 5/1995 | Holmes | |
| 5,437,669 A | 8/1995 | Yuan et al. | |
| 5,437,672 A | 8/1995 | Alleyne | |
| 5,439,464 A | 8/1995 | Shapiro | |
| 5,443,516 A | 8/1995 | Albrektsson et al. | |
| 5,456,722 A | 10/1995 | Mcleod et al. | |
| 5,458,641 A | 10/1995 | Ramirez Jimenez | |
| 5,458,642 A | 10/1995 | Beer et al. | |
| 5,458,643 A | 10/1995 | Oka et al. | |
| 5,464,439 A | 11/1995 | Gendler | |
| 5,470,333 A | 11/1995 | Ray | |
| 5,476,463 A | 12/1995 | Boachie-Adjei et al. | |
| 5,480,401 A | 1/1996 | Navas | |
| 5,489,308 A | 2/1996 | Kuslich et al. | |
| 5,496,318 A | 3/1996 | Howland et al. | |
| 5,507,745 A | 4/1996 | Logroscino et al. | |
| 5,507,813 A | 4/1996 | Dowd et al. | |
| 5,514,180 A | 5/1996 | Heggeness et al. | |
| 5,522,899 A | 6/1996 | Michelson | |
| 5,527,312 A | 6/1996 | Ray | |
| 5,531,745 A | 7/1996 | Ray | |
| 5,531,747 A | 7/1996 | Ray | |
| 5,534,028 A | 7/1996 | Bao et al. | |
| 5,534,030 A | 7/1996 | Navarro et al. | |
| 5,534,031 A | 7/1996 | Matsuzaki et al. | |
| 5,540,688 A | 7/1996 | Navas | |
| 5,545,166 A | 8/1996 | Howland | |
| 5,545,229 A | 8/1996 | Parsons et al. | |
| 5,549,607 A | 8/1996 | Olson et al. | |
| 5,556,431 A | 9/1996 | Buttner-Janz | |
| 5,556,687 A | 9/1996 | McMillin | |
| 5,562,735 A | 10/1996 | Margulies | |
| 5,562,736 A | 10/1996 | Ray et al. | |
| 5,562,737 A | 10/1996 | Graf | |
| 5,569,248 A | 10/1996 | Mathews | |
| 5,571,189 A | 11/1996 | Kuslich | |
| 5,571,191 A | 11/1996 | Fitz | |
| 5,572,191 A | 11/1996 | Lundberg | |
| 5,582,612 A | 12/1996 | Lin | |
| 5,584,832 A | 12/1996 | Schlapfer | |
| 5,603,713 A | 2/1997 | Aust et al. | |
| 5,609,634 A | 3/1997 | Voydeville | |
| 5,613,968 A * | 3/1997 | Lin | 606/320 |
| 5,645,597 A | 7/1997 | Krapiva | |
| 5,645,599 A | 7/1997 | Samani | |
| 5,649,926 A | 7/1997 | Howland | |
| 5,653,762 A | 8/1997 | Pisharodi | |
| 5,666,243 A | 9/1997 | Brent | |
| 5,672,175 A | 9/1997 | Martin | |
| 5,674,295 A | 10/1997 | Ray et al. | |
| 5,674,296 A | 10/1997 | Bryan et al. | |
| 5,676,701 A | 10/1997 | Yuan et al. | |
| 5,681,310 A | 10/1997 | Yuan et al. | |
| 5,683,464 A | 11/1997 | Wagner et al. | |
| 5,683,465 A | 11/1997 | Shinn et al. | |
| 5,688,272 A | 11/1997 | Montague et al. | |
| 5,690,629 A | 11/1997 | Asher et al. | |
| 5,702,392 A | 12/1997 | Wu et al. | |
| 5,702,450 A | 12/1997 | Bisserie | |
| 5,702,453 A | 12/1997 | Rabbe et al. | |
| 5,704,936 A | 1/1998 | Mazel | |
| 5,713,900 A | 2/1998 | Benzel et al. | |
| 5,716,415 A | 2/1998 | Steffee | |
| 5,725,582 A | 3/1998 | Bevan et al. | |
| 5,728,097 A | 3/1998 | Mathews | |
| 5,735,899 A | 4/1998 | Schwartz et al. | |
| 5,749,873 A | 5/1998 | Fairley | |
| 5,755,796 A | 5/1998 | Ibo et al. | |
| 5,772,661 A | 6/1998 | Michelson | |
| 5,797,909 A | 8/1998 | Michelson | |
| 5,800,435 A * | 9/1998 | Errico et al. | 606/261 |
| 5,814,046 A | 9/1998 | Hopf | |
| 5,824,093 A | 10/1998 | Ray et al. | |
| 5,824,094 A | 10/1998 | Serhan et al. | |
| 5,836,948 A | 11/1998 | Zucherman et al. | |
| 5,860,977 A | 1/1999 | Zucherman et al. | |
| 5,865,846 A | 2/1999 | Bryan et al. | |
| 5,868,745 A | 2/1999 | Alleyne | |
| 5,876,404 A | 3/1999 | Zucherman et al. | |
| 5,888,223 A | 3/1999 | Bray, Jr. | |
| 5,893,889 A | 4/1999 | Harrington | |
| RE36,221 E | 6/1999 | Breard et al. | |
| 5,916,267 A | 6/1999 | Tienboon | |
| 5,951,555 A | 9/1999 | Rehak et al. | |
| 5,961,516 A | 10/1999 | Graf | |
| 5,986,169 A | 11/1999 | Gjunter | |
| 6,001,130 A | 12/1999 | Bryan et al. | |
| 6,004,322 A | 12/1999 | Bernstein | |
| 6,014,588 A | 1/2000 | Fitz | |
| 6,019,759 A | 2/2000 | Rogozinski | |
| 6,019,792 A | 2/2000 | Cauthen | |
| 6,039,761 A | 3/2000 | Li et al. | |
| 6,039,763 A | 3/2000 | Shelokov | |
| 6,048,342 A | 4/2000 | Zucherman et al. | |
| 6,063,088 A | 5/2000 | Winslow | |
| 6,063,121 A | 5/2000 | Xavier et al. | |
| 6,066,325 A | 5/2000 | Wallace et al. | |
| 6,068,630 A | 5/2000 | Zucherman et al. | |

| | | | |
|---|---|---|---|
| RE36,758 E | 6/2000 | Fitz | |
| 6,074,390 A | 6/2000 | Zucherman et al. | |
| 6,080,157 A | 6/2000 | Cathro et al. | |
| 6,090,112 A | 7/2000 | Zucherman et al. | |
| 6,093,205 A | 7/2000 | McLeod et al. | |
| 6,113,637 A | 9/2000 | Gill et al. | |
| 6,113,639 A | 9/2000 | Ray et al. | |
| 6,132,464 A | 10/2000 | Martin | |
| 6,132,465 A | 10/2000 | Ray et al. | |
| 6,146,383 A * | 11/2000 | Studer et al. | 606/308 |
| 6,146,421 A | 11/2000 | Gordon et al. | |
| 6,149,652 A | 11/2000 | Zucherman et al. | |
| 6,151,934 A | 11/2000 | Chong et al. | |
| 6,152,926 A | 11/2000 | Zucherman et al. | |
| 6,156,038 A | 12/2000 | Zucherman et al. | |
| 6,156,067 A | 12/2000 | Bryan et al. | |
| 6,176,861 B1 | 1/2001 | Bernstein et al. | |
| 6,179,838 B1 | 1/2001 | Fiz | |
| 6,183,471 B1 | 2/2001 | Zucherman et al. | |
| 6,187,005 B1 * | 2/2001 | Brace et al. | 606/264 |
| 6,190,387 B1 | 2/2001 | Zucherman et al. | |
| 6,190,414 B1 | 2/2001 | Young et al. | |
| 6,206,882 B1 | 3/2001 | Cohen | |
| 6,206,922 B1 | 3/2001 | Zdeblick et al. | |
| 6,228,118 B1 | 5/2001 | Gordon | |
| 6,235,030 B1 | 5/2001 | Zucherman et al. | |
| 6,238,397 B1 | 5/2001 | Zucherman et al. | |
| 6,241,730 B1 | 6/2001 | Alby | |
| 6,264,655 B1 | 7/2001 | Pisharodi | |
| 6,267,764 B1 | 7/2001 | Elberg | |
| 6,280,444 B1 | 8/2001 | Zucherman et al. | |
| 6,290,700 B1 | 9/2001 | Schmotzer | |
| 6,293,949 B1 | 9/2001 | Justis et al. | |
| 6,312,469 B1 | 11/2001 | Gielen et al. | |
| 6,314,325 B1 | 11/2001 | Fitz | |
| 6,332,882 B1 | 12/2001 | Zucherman et al. | |
| 6,332,883 B1 | 12/2001 | Zucherman et al. | |
| 6,379,355 B1 | 4/2002 | Zucherman et al. | |
| 6,402,750 B1 | 6/2002 | Atkinson et al. | |
| 6,413,259 B1 | 7/2002 | Lyons et al. | |
| 6,419,676 B1 | 7/2002 | Zucherman et al. | |
| 6,419,677 B2 | 7/2002 | Zucherman et al. | |
| 6,419,703 B1 | 7/2002 | Fallin et al. | |
| 6,419,704 B1 | 7/2002 | Ferree | |
| 6,440,169 B1 | 8/2002 | Elberg et al. | |
| 6,447,546 B1 | 9/2002 | Bramlet et al. | |
| 6,451,019 B1 | 9/2002 | Zucherman et al. | |
| 6,451,020 B1 | 9/2002 | Zucherman et al. | |
| 6,458,131 B1 | 10/2002 | Ray | |
| 6,461,359 B1 | 10/2002 | Tribus et al. | |
| 6,471,704 B2 | 10/2002 | Gertzbein et al. | |
| 6,475,219 B1 | 11/2002 | Shelokov | |
| 6,478,796 B2 | 11/2002 | Zucherman et al. | |
| 6,481,440 B2 | 11/2002 | Gielen et al. | |
| 6,485,518 B1 | 11/2002 | Cornwall et al. | |
| 6,500,178 B2 | 12/2002 | Zucherman et al. | |
| 6,514,256 B2 | 2/2003 | Zucherman et al. | |
| 6,527,806 B2 | 3/2003 | Ralph et al. | |
| 6,540,747 B1 | 4/2003 | Marino | |
| 6,540,785 B1 | 4/2003 | Gill et al. | |
| 6,565,605 B2 | 5/2003 | Goble et al. | |
| 6,579,319 B2 | 6/2003 | Goble et al. | |
| 6,582,433 B2 | 6/2003 | Yun | |
| 6,585,769 B1 | 7/2003 | Muhanna et al. | |
| 6,610,091 B1 | 8/2003 | Reiley | |
| 6,616,669 B2 | 9/2003 | Ogilvie et al. | |
| 6,626,909 B2 | 9/2003 | Chin | |
| 6,626,944 B1 | 9/2003 | Taylor | |
| 6,652,527 B2 | 11/2003 | Zucherman et al. | |
| 6,652,534 B2 | 11/2003 | Zucherman et al. | |
| 6,652,585 B2 | 11/2003 | Lange | |
| 6,669,729 B2 | 12/2003 | Chin | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,733,534 B2 | 5/2004 | Sherman | |
| 6,761,719 B2 | 7/2004 | Justis et al. | |
| 6,761,720 B1 | 7/2004 | Senegas | |
| 6,783,527 B2 | 8/2004 | Drewry et al. | |
| 6,796,983 B1 | 9/2004 | Zucherman et al. | |
| 6,811,567 B2 | 11/2004 | Reiley | |
| 6,835,205 B2 | 12/2004 | Atkinson et al. | |
| 6,835,207 B2 | 12/2004 | Zacouto et al. | |
| 7,491,221 B2 * | 2/2009 | David | 606/288 |
| 7,615,068 B2 * | 11/2009 | Timm et al. | 606/266 |
| 7,662,175 B2 * | 2/2010 | Jackson | 606/300 |
| 2001/0007073 A1 | 7/2001 | Zucherman et al. | |
| 2001/0012938 A1 | 8/2001 | Zucherman et al. | |
| 2001/0016743 A1 | 8/2001 | Zucherman et al. | |
| 2001/0021850 A1 | 9/2001 | Zucherman et al. | |
| 2001/0031965 A1 | 10/2001 | Zucherman et al. | |
| 2001/0039452 A1 | 11/2001 | Zucherman et al. | |
| 2002/0029039 A1 | 3/2002 | Zucherman et al. | |
| 2002/0065557 A1 | 5/2002 | Goble et al. | |
| 2002/0072800 A1 | 6/2002 | Goble et al. | |
| 2002/0091446 A1 | 7/2002 | Zucherman et al. | |
| 2002/0099384 A1 | 7/2002 | Scribner et al. | |
| 2002/0116000 A1 | 8/2002 | Zucherman et al. | |
| 2002/0123806 A1 | 9/2002 | Reiley | |
| 2002/0143331 A1 | 10/2002 | Zucherman et al. | |
| 2002/0143341 A1 * | 10/2002 | Biedermann et al. | 606/73 |
| 2002/0151895 A1 | 10/2002 | Soboleski et al. | |
| 2002/0183746 A1 | 12/2002 | Zucherman et al. | |
| 2003/0004572 A1 | 1/2003 | Goble et al. | |
| 2003/0009226 A1 | 1/2003 | Graf | |
| 2003/0028191 A1 * | 2/2003 | Shluzas | 606/61 |
| 2003/0028250 A1 | 2/2003 | Reiley et al. | |
| 2003/0040797 A1 | 2/2003 | Fallin et al. | |
| 2003/0055427 A1 | 3/2003 | Graf | |
| 2003/0065330 A1 | 4/2003 | Zucherman et al. | |
| 2003/0073998 A1 | 4/2003 | Pagliuca et al. | |
| 2003/0109880 A1 | 6/2003 | Shirado et al. | |
| 2003/0153912 A1 | 8/2003 | Graf | |
| 2003/0191470 A1 | 10/2003 | Ritland | |
| 2003/0220642 A1 | 11/2003 | Freudiger | |
| 2003/0220643 A1 | 11/2003 | Ferree | |
| 2004/0006341 A1 | 1/2004 | Shaolian et al. | |
| 2004/0006342 A1 * | 1/2004 | Altarac et al. | 606/61 |
| 2004/0006391 A1 | 1/2004 | Reiley | |
| 2004/0024458 A1 | 2/2004 | Senegas et al. | |
| 2004/0049189 A1 | 3/2004 | Le Couedic et al. | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0073215 A1 | 4/2004 | Carli | |
| 2004/0078082 A1 | 4/2004 | Lange | |
| 2004/0082954 A1 | 4/2004 | Teitelbaum et al. | |
| 2004/0087950 A1 | 5/2004 | Teitelbaum | |
| 2004/0106995 A1 | 6/2004 | Le Couedic et al. | |
| 2004/0111154 A1 | 6/2004 | Reiley | |
| 2004/0116927 A1 | 6/2004 | Graf | |
| 2004/0117017 A1 | 6/2004 | Pasquet et al. | |
| 2004/0127989 A1 | 7/2004 | Dooris et al. | |
| 2004/0143264 A1 | 7/2004 | Mcafee | |
| 2004/0147928 A1 | 7/2004 | Landry et al. | |
| 2004/0153071 A1 | 8/2004 | Zucherman et al. | |
| 2004/0158245 A1 | 8/2004 | Chin | |
| 2004/0167520 A1 | 8/2004 | Zucherman et al. | |
| 2004/0172025 A1 | 9/2004 | Drewry et al. | |
| 2004/0181282 A1 | 9/2004 | Zucherman et al. | |
| 2004/0181285 A1 | 9/2004 | Simonson | |
| 2004/0186475 A1 | 9/2004 | Falahee | |
| 2004/0220568 A1 | 11/2004 | Zucherman et al. | |
| 2004/0225289 A1 | 11/2004 | Biedermann et al. | |
| 2004/0230192 A1 | 11/2004 | Graf | |
| 2004/0230201 A1 | 11/2004 | Yuan et al. | |
| 2004/0230304 A1 | 11/2004 | Yuan et al. | |
| 2004/0236327 A1 | 11/2004 | Paul et al. | |
| 2004/0236328 A1 | 11/2004 | Paul et al. | |
| 2004/0236329 A1 | 11/2004 | Panjabi | |
| 2004/0243239 A1 | 12/2004 | Taylor | |
| 2005/0010291 A1 | 1/2005 | Stinson et al. | |

| | | | |
|---|---|---|---|
| 2005/0010293 A1 | 1/2005 | Zucherman et al. | |
| 2005/0010298 A1 | 1/2005 | Zucherman et al. | |
| 2005/0027361 A1 | 2/2005 | Reiley | |
| 2005/0033434 A1 | 2/2005 | Berry | |
| 2005/0033439 A1 | 2/2005 | Gordon et al. | |
| 2005/0043797 A1 | 2/2005 | Lee | |
| 2005/0043799 A1 | 2/2005 | Reiley | |
| 2005/0070899 A1 | 3/2005 | Doubler | |
| 2005/0070901 A1* | 3/2005 | David | 606/61 |
| 2005/0096654 A1* | 5/2005 | Lin | 606/61 |
| 2005/0101954 A1* | 5/2005 | Simonson | 606/61 |
| 2005/0113927 A1 | 5/2005 | Malek | |
| 2005/0119748 A1 | 6/2005 | Reiley et al. | |
| 2005/0131406 A1 | 6/2005 | Reiley et al. | |
| 2005/0131545 A1* | 6/2005 | Chervitz et al. | 623/17.14 |
| 2005/0137705 A1 | 6/2005 | Reiley | |
| 2005/0137706 A1 | 6/2005 | Reiley | |
| 2005/0143818 A1 | 6/2005 | Yuan et al. | |
| 2005/0149190 A1 | 7/2005 | Reiley | |
| 2005/0154467 A1 | 7/2005 | Peterman et al. | |
| 2005/0177166 A1 | 8/2005 | Timm | |
| 2005/0192572 A1* | 9/2005 | Abdelgany et al. | 606/61 |
| 2006/0025770 A1* | 2/2006 | Schlapfer et al. | 606/61 |
| 2006/0217718 A1* | 9/2006 | Chervitz et al. | 606/61 |
| 2006/0229606 A1* | 10/2006 | Clement et al. | 606/61 |
| 2006/0247624 A1* | 11/2006 | Banouskou et al. | 606/61 |
| 2006/0282074 A1 | 12/2006 | Renaud et al. | |

FOREIGN PATENT DOCUMENTS

| | | |
|---|---|---|
| EP | 322334 B1 | 2/1992 |
| EP | 667127 A1 | 8/1995 |
| EP | 767637 B1 | 11/1998 |
| EP | 768843 B1 | 2/1999 |
| EP | 669109 B1 | 5/1999 |
| EP | 1239785 B1 | 9/2004 |
| EP | 1343424 B1 | 9/2004 |
| EP | 1399078 B1 | 12/2004 |
| FR | 2721501 B1 | 8/1996 |
| JP | 10179622 A2 | 7/1998 |
| JP | 10277070 A2 | 10/1998 |
| SU | 1468543 A1 | 3/1989 |
| SU | 1517953 A1 | 10/1989 |
| WO | WO8707827 A1 | 12/1987 |
| WO | WO9421185 A1 | 9/1994 |
| WO | WO9505783 A1 | 3/1995 |
| WO | WO9505784 A1 | 3/1995 |
| WO | WO9505785 A1 | 3/1995 |
| WO | WO9505786 A1 | 3/1995 |
| WO | WO9600049 A1 | 1/1996 |
| WO | WO9822033 A1 | 5/1998 |
| WO | WO9848707 A1 | 11/1998 |
| WO | WO9848717 A1 | 11/1998 |
| WO | WO9856301 A1 | 12/1998 |
| WO | WO9905995 A1 | 2/1999 |
| WO | WO9921500 A1 | 5/1999 |
| WO | WO9921501 A1 | 5/1999 |
| WO | WO9923963 A1 | 5/1999 |
| WO | WO9965412 A1 | 12/1999 |
| WO | WO9960957 C2 | 5/2000 |
| WO | WO0038582 | 7/2000 |
| WO | WO0062684 A1 | 10/2000 |
| WO | WO0130248 A1 | 5/2001 |
| WO | WO0145576 A1 | 6/2001 |
| WO | WO0149192 A1 | 7/2001 |
| WO | WO0156489 A1 | 8/2001 |
| WO | WO0164142 A1 | 9/2001 |
| WO | WO0164144 A2 | 9/2001 |
| WO | WO0191657 A1 | 12/2001 |
| WO | WO0191658 A1 | 12/2001 |
| WO | WO0197721 A2 | 12/2001 |
| WO | WO0197721 A3 | 12/2001 |
| WO | WO0200124 A1 | 1/2002 |
| WO | WO0203882 A2 | 1/2002 |
| WO | WO0207621 A1 | 1/2002 |
| WO | WO0207622 A1 | 1/2002 |
| WO | WO0207623 A1 | 1/2002 |
| WO | WO0213732 A3 | 2/2002 |
| WO | WO0230336 A2 | 4/2002 |
| WO | WO0234120 A2 | 5/2002 |
| WO | WO0243603 A1 | 6/2002 |
| WO | WO02067792 A2 | 9/2002 |
| WO | WO02067793 A2 | 9/2002 |
| WO | WO02089712 A1 | 11/2002 |
| WO | WO02089712 A2 | 11/2002 |
| WO | WO02102259 A2 | 12/2002 |
| WO | WO03009737 A1 | 2/2003 |
| WO | WO03011147 A1 | 2/2003 |
| WO | WO03015646 A2 | 2/2003 |
| WO | WO03045262 A2 | 6/2003 |
| WO | WO03077806 A1 | 9/2003 |
| WO | WO2004017817 A2 | 3/2004 |
| WO | WO2004019762 A2 | 3/2004 |
| WO | WO2004024010 A1 | 3/2004 |
| WO | WO2004032794 A2 | 4/2004 |
| WO | WO2004032794 A3 | 4/2004 |
| WO | WO2004039239 A2 | 5/2004 |
| WO | WO2004039239 A3 | 5/2004 |
| WO | WO2004039243 A2 | 5/2004 |
| WO | WO2004039243 A3 | 5/2004 |
| WO | WO2004041066 A2 | 5/2004 |
| WO | WO2004041066 A3 | 5/2004 |
| WO | WO2004073533 A1 | 9/2004 |
| WO | WO2004098423 A1 | 11/2004 |
| WO | WO2004098452 A2 | 11/2004 |
| WO | WO2004105577 A2 | 12/2004 |
| WO | WO2004105580 A2 | 12/2004 |
| WO | WO2005013864 A2 | 2/2005 |
| WO | WO2005037149 A2 | 4/2005 |
| WO | WO2005044152 A1 | 5/2005 |

OTHER PUBLICATIONS

Head WC, Wagner surface replacement arthroplasty of the hip. Analysis of fourteen failures in forty-one hips:, J Bone Joint Surg. [Am], Mar. 1981 63:3, PubMed Abstract.

Kotani Y, et al., "The effects of spinal fixation and destabilization on the biomechanical and histologic properties of spinal ligaments. An in vivo study.", Spine, Mar. 15, 1998 23:6, PubMed abstract.

Lemaire JP, et al., "Intervertebral Disc Prosthesis: Results and Prospects for the Year 2000", Clinical Orthopaedics and Related Research, PubMed abstract.

Nagata H, et al., "The effects of immobilization of long segments of the spine on the adjacent and distal facet force and lumbrosacral motioin", Spine, Dec. 1993 18:16. PubMed abstract.

Nibu K, et al., Multidirectional stabilizing potential of BAK interbody spinal fusion system for anterior surgery, J Spinal Discord, Aug. 1997 10:4, PubMed abstract.

Tsantrizos A, et al., "Segmental stability and compressive strength of posterior lumbar interbody fusion implants", Spine, Aug. 1, 2000 25:15, PubMed abstract.

Todd Anres; Facet Joint Arthroplasty: A Glimpse of the Future of Spine Technology, Othopaedic Product News, Sep./Oct. 2005 p. 38,40.

Archus Orthopedics; Total Facet Arthoroplasty System (TFAS™) Website http://www.archususa.com/Product.html.

* cited by examiner

POLYAXIAL ORTHOPEDIC FASTENING APPARATUS WITH INDEPENDENT LOCKING MODES

CROSS-REFERENCE TO RELATED APPLICATIONS

This application is a continuation-in-part of the following: U.S. patent application Ser. No. 11/063,941 filed Feb. 22, 2005 now U.S. Pat. No. 7,993,373 which carries Applicants' docket no. FSI-10 and is entitled POLYAXIAL ORTHOPEDIC FASTENING APPARATUS.

The following disclosure is incorporated herein by reference: U.S. application Ser. No. 10/860,778 filed Jun. 2, 2004 which carries Applicants' docket no. FSI-2 NPROV and is entitled SPINAL FACET IMPLANT WITH SPHERICAL IMPLANT APPOSITION SURFACE AND BONE BED AND METHODS OF USE.

BACKGROUND OF THE INVENTION

1. The Field of the Invention

The present invention relates generally to systems and methods for attaching implants to bone, and more specifically, to a polyaxial orthopedic fastening apparatus particularly useful in the field of facet joint replacement.

2. The Relevant Technology

Orthopedic medicine provides a wide array of implants that can be attached to bone to alleviate various pathologies. One unique challenge in orthopedics is to provide implants and fastening devices that are adaptable to a variety of bone morphologies. Each patient will have a different bone structure; accordingly, it may be necessary to allow for adjustable positioning of an implant with respect to the bone so that the implant will be positioned to perform its function.

For this reason, a number of fixation systems have been invented that enable variation of the angle between the implant and the fastener. Although such fixation systems generally permit adaptation to the bone morphology of a patient to provide secure anchoring of the implant to bone, they are generally somewhat limited in the types of adjustment they permit with respect to the bone. Accordingly, such fixation systems may not be usable with a number of implants that require more comprehensive adjustability. Furthermore, many known implant fixation systems are complex due to the presence of several parts, or due to the need to perform several steps to utilize them to attach an implant to bone. Yet further, some known implant fixation systems are expensive, and require the use of unusual tooling. A need exists in the art for implant fixation systems and methods that alleviate the foregoing shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

The present invention advances the state of the art by providing systems and methods that can be used to anchor orthopedic implants to bone in a manner that provides a high degree of implant adjustability, simplicity, and ease of use. The present invention can be used in any orthopedic procedure, but may have particular utility in the field of facet joint replacement to alleviate back pain resulting from traumatic, inflammatory, metabolic, synovial, neoplastic and degenerative spinal disorders. The configuration and operation of selected embodiments of the invention will be shown and described in greater detail with reference to FIGS. 1 through 4, as follows.

In this application, the terms "fastener," "interpositional member," and "engagement member" are used broadly. A "fastener" generally relates to one or more members that can be used to "lock" two other objects together by restricting relative rotation and/or translation about or along at least one axis. More precisely, a "rotational fastener" is a fastener that restricts relative rotation of the two objects. A "translational" fastener is a fastener that restricts relative translation of the two objects. An "interpositional member" generally is a member, at least part of which is designed to be positioned between at least two other members of a system. An "engagement member" is a member that is movable into and/or out of contact with another member to accomplish a function such as locking the members together.

"Polyaxial" rotation is rotation that can occur about at least two axes that are not parallel to each other. "Triaxial rotation" is rotation about three perpendicular axes. Triaxial rotation is equivalent to rotation about a point, because free rotation about any axis of a 3D coordinate system is the same as rotation that is not limited to any axis in the system.

Figure 1:
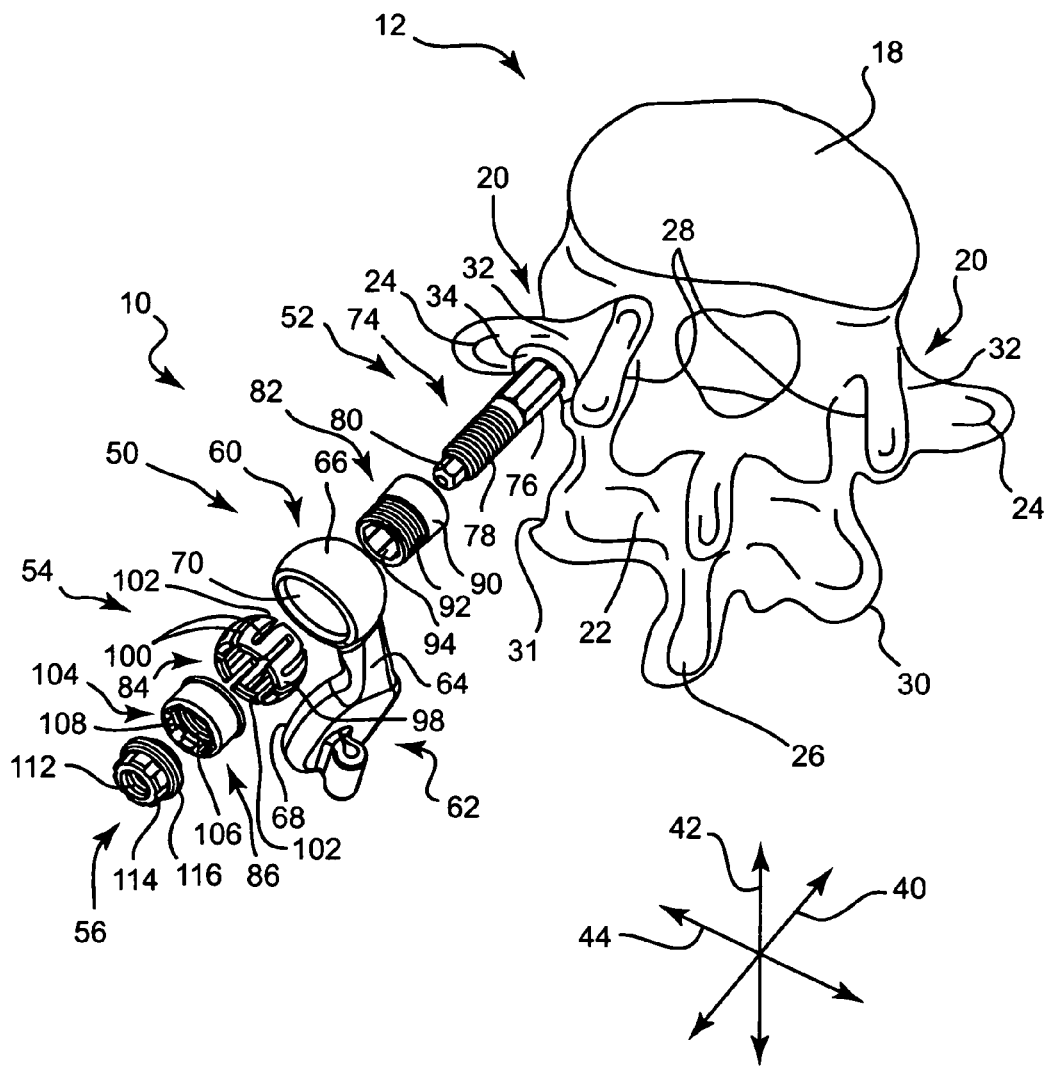
FIG. 1 is an exploded, perspective view of a vertebra with an apparatus according to one embodiment of the invention, with the apparatus positioned to attach an implant to the vertebra.

Referring to FIG. 1, a perspective view illustrates an apparatus 10 according to one embodiment of the invention, in use with a vertebra 12, such as an L4 lumbar vertebra of a human spine. As shown, the vertebra 12 has a body 18, which is generally disc-shaped. The vertebra 12 also has two pedicles 20 extending from the body 18, and a posterior arch, or lamina 22, which extends between the posterior ends of the pedicles 20 to couple the pedicles 20 together. The vertebra 12 also has a pair of transverse processes 24 that extend laterally from the pedicles 20, and a spinous process 26 that extends posteriorly from the lamina 22.

The vertebra 12 also has a pair of superior facets 28, which are positioned toward the top of the vertebra 12 and face generally medially. Additionally, the vertebra 12 has an inferior facet 30, which is positioned toward the bottom of the vertebra 12 and faces generally laterally. A resected inferior facet 31 also faces generally laterally. The articular surface of the resected inferior facet 31 may optionally have been resected away to prepare the resected inferior facet 31 for arthroplasty. Each of the pedicles 20 of the vertebra 12 has a saddle point 32, which is positioned generally at the center of the juncture of each superior facet 28 with the adjacent transverse process 24.

The superior facets 28 of the vertebra 12 articulate (i.e., slide and/or press) against the inferior facets (not shown) of an adjacent superior vertebra (not shown), such as an L3 lumbar vertebra, to limit relative motion between the vertebra 12 and the superior vertebra. Thus, the combination of each superior facet 28 with the adjacent inferior facet defines a facet joint (not shown). Accordingly, two facet joints span the distance between each adjacent pair of vertebrae. The inferior facets 30 of the vertebra 30 are part of other facet joints that control motion between the vertebra 12 and an adjacent inferior vertebra (not shown), such as an L5 lumbar vertebra or the sacrum.

Each of the facet joints may be covered by a capsule (not shown) containing a fluid (not shown) that reduces wear of the facets 28, 30 and facilitates articulation. Additionally, layers of cartilage (not shown) may cover the facets 28, 30 to further reduce wear and facilitate articulation. These anatomical structures, as well as the various muscles, ligaments, and nerves of the spine, will not be depicted in the Figures to enhance the clarity of the disclosure. Such structures may be removed or displaced according to known methods to provide the necessary access to the vertebra 12.

As shown, a semispherical resection 34 has been formed on one of the saddle points 32 of the vertebra 12. The semispherical resection 34 is shaped to receive an implant to replace the articular surface of one or both of the adjacent superior and inferior facets 28, 30. The semispherical resection 34 permits relative rotation between the implant and the vertebra 12 about three perpendicular axes prior to fixation of the implant to the vertebra 12. The axes may be defined as shown by reference numerals 40, 42, and 44 in FIG. 1.

More precisely, the axes may include a first axis 40, a second axis 42, and a third axis 44. The first axis 40 is generally collinear with the axis of the corresponding pedicle 20. The second axis 42 is generally vertical (i.e., parallel to the axis of the body 18) and perpendicular to the first axis 40. The third axis 44 is generally horizontal (i.e., parallel to the end plates of the body 18) and perpendicular to the first and second axes 40, 42.

The apparatus 10 includes an implant 50, a fixation member 52, a rotational fastener 54, and a translational fastener 56. The implant 50 is designed to seat against the semispherical resection 34 and to replace the removed articular surface of the resected inferior facet 31 immediately inferior to it. The fixation member 52 may take the form of a pedicle screw designed to be implanted in the corresponding pedicle 20 to anchor the implant 50 in place. The orthopedic fastener 54 is designed to be coupled to the fixation member 52 to hold the implant against the vertebra 12.

In the embodiment of FIG. 1, the implant 50 has a fixation portion 60, an articulation portion 62, and a stem 64. The fixation portion 60 is shaped to be attached to the semispherical resection 34, and the articulation portion 62 provides a surface that articulates with an adjacent vertebral facet to carry out the function of the inferior facet 30. The articulation portion 62 is coupled to the fixation portion 60 by the stem 64.

As shown, the fixation portion 60 has a bone apposition surface 66, which may be generally semispherical to correspond to the shape of the semispherical resection 34. The fixation portion 60 also has an aperture (not visible in FIG. 1) that passes through the bone apposition surface 66 to receive the fixation member 52. The aperture is somewhat larger than the exterior surface of the fixation member 52 so that the bone apposition surface 66 is able to slide against the semispherical resection 34 with the fixation member 52 in place, implanted in the pedicle 20.

The articulation portion 62 similarly has an articulation surface 68 designed to articulate with a superior facet of a vertebra (or sacrum) immediately inferior to the vertebra 12. The articulation surface 68 may have a convex shape, which may further be semispherical, semicylindrical, or the like. The articulation surface 68 may be designed to articulate with a natural superior facet and/or a prosthetic superior facet.

In addition to the bone apposition surface 66, the fixation portion 60 also has an engagement surface 70 shaped to receive the rotational fastener 54 such that the rotational fastener 54 is able to restrict relative rotation between the implant 50 and the fixation member 52. The engagement surface 70 has a generally semispherical concave shape through which the aperture (not shown) of the fixation portion 60 passes.

In the embodiment of FIG. 1, the fixation member 52 has a distal end (not visible in FIG. 1) 74 implanted into the corresponding pedicle 20 of the vertebra 12, and a proximal end 74 that protrudes from the corresponding saddle point 32. The distal end has threads that facilitate implantation of the distal end 74 in the pedicle 20 and keep the implanted distal end in place. The fixation member 52 also has a sliding interface 76 positioned between the distal end and the proximal end 76. The sliding interface 76 may have a polygonal or other non-circular cross section shaped to receive the rotational fastener 54 in such a manner that no significant relative rotation can occur between the sliding interface 76 and the rotational fastener 54.

The proximal end 74 has a plurality of threads 78 that are exposed to receive the fastener 54. Additionally, the proximal end 74 has a torquing interface 80 that may be used to apply torque to the fixation member 52 to implant the distal end in the pedicle 20. The torquing interface 80 may take the form of a hexagonal recess or projection that mates with a corresponding hexagonal feature on a driver (not shown).

As shown, the rotational fastener 54 includes an interpositional member 82, an engagement member 84, and a rotational locking member 86. The interpositional member 82 may have a generally tubular shape with a tapered portion 90, a plurality of threads 92 adjacent to the tapered portion 90, and an interface 94. As shown, the tapered portion 90 becomes narrower toward the threads 92. The interface 94 is designed to provide a slidable, yet non-rotating connection between the interpositional member 82 and the sliding interface 76 of the fixation member 52. Accordingly, the interface 94 may take the form of a bore with a polygonal cross section that receives the corresponding polygonal cross section of the sliding interface 76 with enough clearance to permit relatively free sliding motion. Alternatively, a tighter fit may be used to restrict sliding, but permit relative translation between the interpositional member 82 and the fixation member 52 under the application of force.

As also illustrated in FIG. 1, the engagement member 84 is generally spherical in shape, with a hollow interior. The hollow interior has a taper that generally matches the taper of the tapered portion 90 of the interpositional member 82. The engagement member 84 has an implant engagement surface 98 with a semispherical shape, and a plurality of grooves 100 arranged in a parallel, substantially radially symmetrical fashion about the implant engagement surface 98. The grooves 98 permit expansion and contraction of the implant engagement surface 98. The hollow interior is accessible via ports 102 positioned at either end of the implant engagement surface 98.

The rotational locking member 86 has a bore 104 in which a plurality of threads 106 are formed. The threads 106 are designed to mate with the threads 92 of the interpositional member 82. The bore 104 also has a torquing interface 108 formed therein to facilitate rotation of the rotational locking member 86 into engagement with the interpositional member 82. The torquing interface 108 may take the form of a portion of the bore 104 having a generally polygonal cross sectional shape, such as a hegaxonal cross sectional shape. Thus, a corresponding hexagonal protrusion of a driver (not shown)

may be inserted into the torquing interface 108 to rotate the rotational locking member 86 into engagement with the interpositional member 82.

The translational fastener 56, which may also be termed a translational locking member, has a threaded bore 112, a torquing interface 114, and a flange 116. The threads of the threaded bore 112 are sized to rotate into engagement with the threads 78 of the proximal end 74 of the fixation member 52. The torquing interface 114 may take the form of a protrusion having a generally hexagonal shape capable of being received within a recess of a driver (not shown) having a corresponding hexagonal shape.

The flange 116 protrudes generally radially from the exterior of the translational fastener 56, adjacent to the torquing interface 114. The flange 116 may be sized to abut the adjoining annular surface of the rotational locking member 86 to enable the translational fastener 56 to exert relatively uniform, linear force against the rotational locking member 86 upon tightening of the translational fastener 56. If desired, a portion of the translational fastener 56 may nest within the bore 104 of the rotational locking member 86 to reduce the profile of the assembled apparatus 10.

The apparatus 10 may be secured to the vertebra 12 according to a variety of methods. According to one method, the fixation member 52 is first implanted in the corresponding pedicle 20. This may be carried by, for example, forming an incision in the overlying tissues, retracting the tissues from the operating area, implanting a guide wire in the pedicle 20 under fluoroscopy, and then rotating the fixation member 52 into engagement with the pedicle 20 through the use of a driver (not shown) coupled to the torquing interface 80.

Through the use of the rotational fastener 54 and the translational fastener 56, the orientation of the implant 50 and the position of the implant 50 along the fixation member 52 (i.e., along the first axis 40) may be independently locked. The rotational fastener 54 and the implant 50 may first be assembled together by assembling the interpositional member 82, the engagement member 84, the rotational locking member 86, and the implant 50.

The engagement member 84 may first be inserted into the hollow interior of the fixation portion 60 of the implant 50. Since the engagement member 84 has not yet been significantly expanded, there is clearance between the implant engagement surface 98 of the engagement member 84 and the engagement surface 70 of the fixation portion 60 of the implant 50. This clearance permits rotation of the engagement member 84 within the fixation portion 60. The engagement surface 70 of the fixation portion 60 may have a semispherical shape that extends far enough to effectively capture the engagement member 84. Accordingly, the engagement member 84 may need to be compacted and/or pressed into the hollow interior of the fixation portion 60.

The interpositional member 82 is then inserted through the aperture (not shown) of the fixation portion 60 and into the hollow interior of the engagement member 84 such that the tapered portion 90 extends through the port 102 that will be oriented toward the fixation member 52, and the threads 92 extend through the other port 102 (i.e., the port 102 that will be oriented toward the translational fastener 56 and the rotational locking member 86, as shown in the exploded view of FIG. 1). Then, the rotational locking member 86 is positioned adjacent to the corresponding port 102 such that the threads 92 enter the bore 104.

The rotational locking member 86 is rotated with respect to the interpositional member 82 such that the threads 106 of the bore 104 engage the threads 92 of the interpositional member 82. Continued rotation of the rotational locking member 86 with respect to the interpositional member 82 will cause the engagement member 84 to expand as the opposite port 102 slides toward the larger end of the tapered portion 90. However, at this stage, the rotational fastener 54 remains in the unlocked configuration because the rotational locking member 86 is only rotated sufficiently to engage the threads 92 to keep the rotational locking member 86, the interpositional member 82, and the engagement member 84 together.

The assembled implant 50 and rotational fastener 54 may then be advanced toward the proximal end 74 of the implanted fixation member 52 such that the torquing interface 80, and then at least some of the threads 78, pass through the interface 94, or bore, of the interpositional member 82. The interface 94 then slides around the sliding interface 76 of the proximal end 74 of the fixation member 52. As mentioned before, some clearance may exist between the sliding interface 76 of the proximal end 74 and the interface 94 of the interpositional member 82. However, the matching polygonal shapes of the sliding interface 76 and the interface 94 prevent relative rotation between the fixation member 52 and the rotational fastener 54.

Since the rotational fastener 54 is still in the unlocked configuration, the implant 50 may be rotated with respect to the fixation member 52 and the vertebra 12. The implant 50 is pivoted generally about the center of the radius of the engagement surface 70 until the articulation surface 68 is properly positioned and oriented to articulate with the corresponding natural or prosthetic superior articulation surface. In the embodiment of FIG. 1, rotation of the implant 50 is not only polyaxial, but also triaxial. Thus, the implant 50 may be rotated about any axis passing through the center of the radius of the engagement surface 70.

Once the implant 50 has been rotated into the proper orientation with respect to the vertebra 12, it may be locked in that orientation by moving the rotational fastener 54 to the locked configuration. The rotational locking member 86 is further rotated with respect to the interpositional member 82, for example, by engaging the torquing interface 108 of the bore 104 with a corresponding feature of a driver (not shown). This rotation urges the opposite port 102 to advance along the tapered portion 90 of the interpositional member 82, toward the larger end of the tapered portion 90. The outward pressure on the port 102 causes the engagement member 84 to expand, thereby increasing the overall radius of the implant engagement surface 98. The implant engagement surface 98 engages the engagement surface 70 of the fixation portion 60 of the implant and exerts outward pressure on the engagement surface 70. As a result, the implant 50 becomes locked to the engagement member 84.

Thus, the rotational fastener 54 has reached the locked configuration, and the implant 50 is no longer rotatable with respect to the vertebra 12. However, the implant 50, together with the rotational fastener 54 that is now rigidly locked to it, may still move along the fixation member 52. The translational fastener 56 may then be applied to restrict such translational motion. More precisely, the translational fastener 56 is moved toward the proximal end 74 of the fixation member 52 such that the threads 78 of the proximal end 74 enter the threaded bore 112 of the translational fastener 56. The translational fastener 56 is rotated to advance the threaded bore 112 along the threads 78 until the flange 116 presses snugly against the adjoining annular surface of the rotational locking member 86. This effectively presses the bone apposition surface 66 of the fixation portion 60 of the implant 50 against the semispherical resection 34 of the corresponding saddle point 32.

Figure 2:
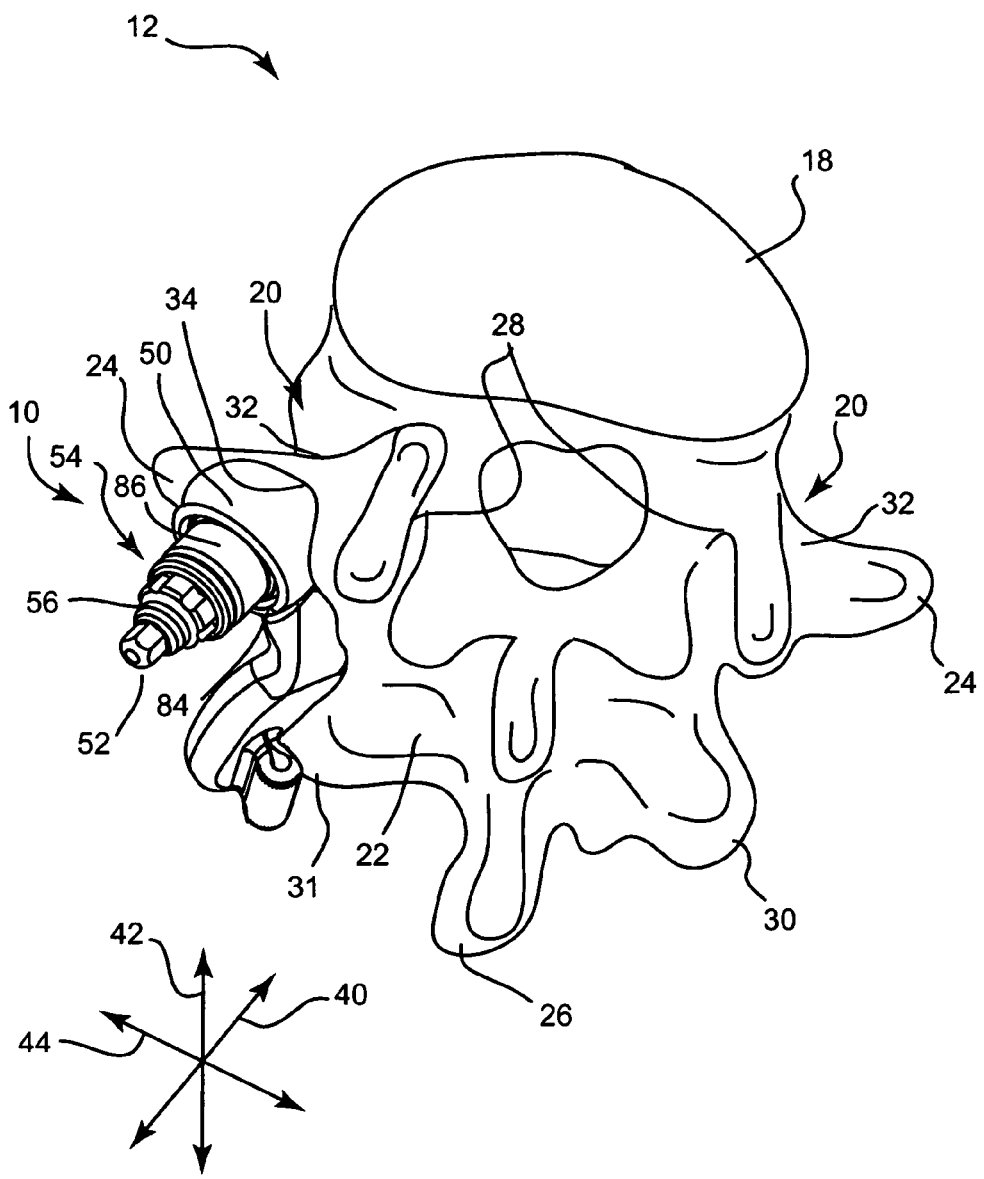
FIG. 2 is a perspective view of the vertebra with the apparatus of FIG. 1 secured to the vertebra in the locked configuration to lock both rotation and translation of the implant.

Referring to FIG. 2, a perspective view illustrates the apparatus 10 in fully assembled form on the vertebra 12. The position and orientation of the implant 50 are fixed with respect to the vertebra 12. Advantageously, since the orientation and position of the implant 50 are independently locked, any subsidence of the bone around the saddle point 32 will not enable the implant 50 to rotate from its desired orientation with respect to the vertebra 12. If such subsidence occurs, the position of the implant 50 may be stabilized with relatively simple revision surgery, i.e., by further tightening the translational fastener 56 or by inserting bone graft, an implant, or some other form of support into the space between the bone apposition surface 66 and the semispherical resection 34.

Those of skill in the art will recognize that an apparatus similar to the apparatus 10 may be applied to the opposite side of the vertebra 12 for bilateral operation. The fixation member 52, rotational fastener 54, and translational fastener 56 may be used to attach left or right, superior and/or inferior, implants to the vertebra 12. In alternative embodiments (not shown), similar components to the components 52, 54, and 56 may even be used to secure nested fixation portions of superior and inferior implants to a single saddle point 32. In yet other alternative embodiments, such similar components may be used to secure other types of implants to the vertebra 12 besides facet joint implants, including but not limited to artificial discs, posterior rod fixation systems, dynamic stabilization systems, and the like (not shown).

Figure 3:
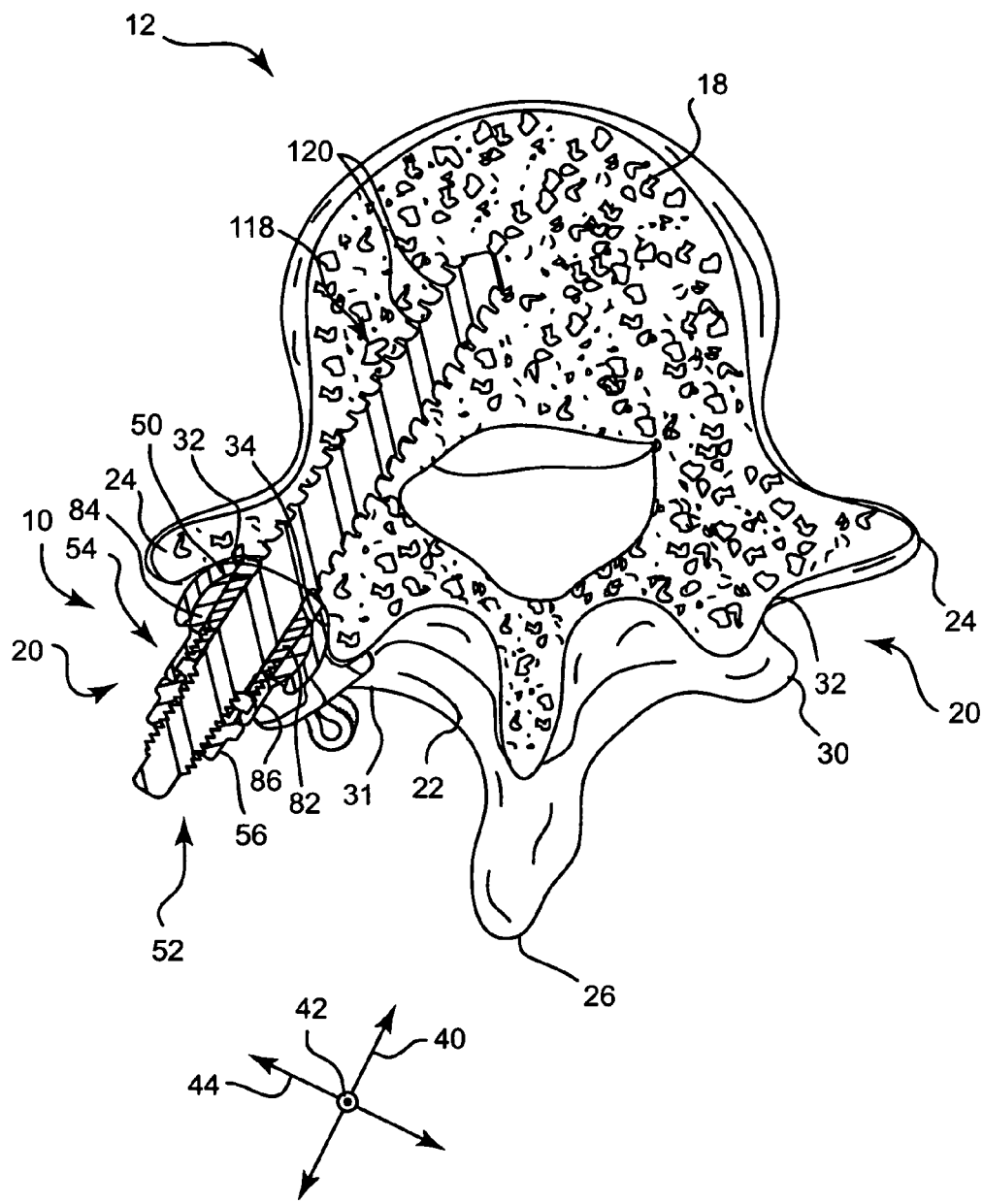
FIG. 3 is a cephalad, section view of the vertebra with the apparatus of FIG. 1 secured to the vertebra in the locked configuration as in FIG. 2.

Referring to FIG. 3, a cephalad, section view illustrates the apparatus 10 in fully assembled form on the vertebra 12. As mentioned previously, the fixation member 52 has a distal end 118 with threads 120 that engage the interior of the corresponding pedicle 20. Another potential advantage to independent rotational and translational locking of the implant 50 is that the purchase of the threads 120 within the pedicle 20 is not significantly challenged by any of the steps used to lock the orientation of the implant 50 with respect to the vertebra 12. Only the axial force exerted by locking of the translational fastener 56 is transmitted to the interface between the threads 120 and the surrounding bone. This decreases the probability that the bone between the threads 120 will fail under shear and permit the distal end 118 to pull free of the bone.

The present invention has particular relevance to orthopedic medicine, and more particularly to facet joint replacement. However, the principles, structures, and methods of the present invention may also be extended to a wide variety of other fields.

The present invention may be embodied in other specific forms without departing from its spirit or essential characteristics. As such the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An apparatus comprising:
an implant;
a fixation member comprising a first interface and a distal end implantable in a bone; and
a rotational fastener comprising a second interface, wherein the second interface is rectilinearly translatable along the first interface, wherein the first and second interfaces have complementary antirotation features,
wherein the apparatus comprises a locked configuration in which the rotational fastener engages the implant in any of a plurality of relative orientations between the implant and the rotational fastener about a first axis to substantially prevent any relative rotation between the implant and the rotational fastener about the first axis;
wherein, in the locked configuration, the rotational fastener is slidably attachable to the fixation member to permit motion of the rotational fastener along the fixation member in a direction nonparallel to the first axis,
wherein the rotational fastener comprises an interpositional member and an engagement member configured to be actuated with respect to the interpositional member to move the rotational fastener from an unlocked configuration to the locked configuration, wherein the engagement member is shaped to expand to move the rotational fastener from the unlocked configuration to the locked configuration, and wherein the rotational fastener further comprises a rotational locking member configured to be advanced along the interpositional member to urge the engagement member to expand, and to keep the rotational fastener in the locked configuration.

2. The apparatus of claim 1, wherein, in the locked configuration, the rotational fastener further engages the implant in any of a plurality of relative orientations between the implant and the rotational fastener about a second axis orthogonal to the first axis and in any of a plurality of relative orientations about a third axis orthogonal to the first and second axes, wherein, in the locked configuration, any relative motion between the implant and the rotational fastener is substantially prevented.

3. The apparatus of claim 1, wherein the engagement member comprises an implant engagement surface having a generally spherical shape, wherein the engagement member comprises a plurality of grooves that permit expansion of the implant engagement surface.

4. The apparatus of claim 1, wherein the interpositional member comprises a tapered shape, wherein the engagement member is configured to expand in response to advancement toward a wider end of the tapered shape.

5. The apparatus of claim 1, further comprising a translational locking member shaped to engage the fixation member to restrict motion of the rotational fastener along the fixation member.

6. The apparatus of claim 1, wherein the bone comprises a vertebra
wherein the implant comprises an articular surface shaped to replace at least a portion of a natural facet articular surface of the vertebra.

7. An apparatus comprising:
an implant;
a fixation member having a first interface and a distal end implantable in a bone; and
a rotational fastener comprising:
an interpositional member comprising a second interface, wherein the second interface is complementary to the first interface with clearance, wherein the first and second interfaces are keyed together to permit translation of the interpositional member along the fixation element and restrict rotation of the interpositional member around the fixation element,
an engagement member configured to be coupled to the interpositional member, the engagement member comprising an implant engagement surface, wherein the engagement member is configured to be actuated with respect to the interpositional member to move the rotational fastener from an unlocked to a locked configuration, and wherein the engagement member is shaped to expand the rotational fastener from the unlocked configuration to the locked configuration; and a rotational locking member configured to be advanced along the interpositional member to urge the engagement member to expand, and to keep the rotational fastener in the locked configuration, wherein the engagement member is expandable to move the implant engagement surface into engagement with the implant to restrict rotation of the implant with respect to the rotational fastener.

8. The apparatus of claim 7, wherein the implant engagement surface is shaped to expand into engagement with the implant in any of a plurality orientations of the engagement member with respect to the implant about a first axis, in any of a plurality of orientations of the engagement member with respect to the implant about a second axis, and in any of a plurality of orientations of the engagement member with respect to the implant about a third axis, wherein the first, second, and third axes are mutually perpendicular, wherein the first, second, and third axes are nonparallel to the direction of translation of the interpositional member along the fixation element.

9. The apparatus of claim 8, wherein the implant engagement surface has a generally spherical shape, wherein the engagement member comprises a plurality of grooves that permit expansion of the implant engagement surface.

10. The apparatus of claim 7, wherein the interpositional member comprises a tapered shape, wherein the engagement member is configured to expand in response to advancement toward a wider end of the tapered shape.

11. The apparatus of claim 7, further comprising a translational locking member shaped to engage the fixation member to restrict motion of the rotational fastener along the fixation member.

12. The apparatus of claim 7, wherein the bone comprises a vertebra, wherein the implant comprises an articular surface shaped to replace at least a portion of a natural facet articular surface of the vertebra.

* * * * *